(12) United States Patent
Zhang et al.

(10) Patent No.: US 12,121,835 B2
(45) Date of Patent: Oct. 22, 2024

(54) METHOD FOR REFINING STYRENE BY USING COMBINED FALLING FILM REBOILERS AND HEAT PUMP TECHNOLOGY TO PROVIDE HEAT SOURCE OF SEPARATION COLUMN

(71) Applicant: Changzhou Ruihua Chemical Engineering Technology Co., Ltd., Suzhou (CN)

(72) Inventors: Jing Zhang, Jiangsu (CN); Chenggang He, Jiangsu (CN); Jiahui Gu, Jiangsu (CN); Haiyan Zhou, Jiangsu (CN); Xia Chen, Jiangsu (CN); Zhigang Xu, Jiangsu (CN)

(73) Assignee: Changzhou Ruihua Chemical Engineering Technology Co., Ltd., Jiangsu (CN)

( * ) Notice: Subject to any disclaimer, the term of this patent is extended or adjusted under 35 U.S.C. 154(b) by 0 days.

(21) Appl. No.: 18/009,541

(22) PCT Filed: Jul. 27, 2022

(86) PCT No.: PCT/CN2022/108063
§ 371 (c)(1),
(2) Date: Dec. 9, 2022

(87) PCT Pub. No.: WO2023/050988
PCT Pub. Date: Apr. 6, 2023

(65) Prior Publication Data
US 2024/0238694 A1    Jul. 18, 2024

(30) Foreign Application Priority Data
Sep. 28, 2021   (CN) .......................... 202111145258.7

(51) Int. Cl.
*B01D 3/32* (2006.01)
*B01D 3/00* (2006.01)
(Continued)

(52) U.S. Cl.
CPC ............. *B01D 3/322* (2013.01); *B01D 3/007* (2013.01); *B01D 3/143* (2013.01); *B01D 5/006* (2013.01); *C07C 7/04* (2013.01)

(58) Field of Classification Search
CPC ........ B01D 3/007; B01D 3/143; B01D 3/322; B01D 5/006; C07C 7/04
See application file for complete search history.

(56) References Cited

U.S. PATENT DOCUMENTS 4,615,769 A * 10/1986 Horigome ................. C07C 7/04
585/800
5,386,075 A * 1/1995 Keil ....................... B01D 3/146
585/800
(Continued)

FOREIGN PATENT DOCUMENTS

CN    1309578 A    8/2001
CN    1163289 C    8/2004
(Continued)

OTHER PUBLICATIONS

GB 32053-2015—Norm of energy consumption per unit product of styrene monomer (10 pages).
(Continued)

*Primary Examiner* — Jonathan Miller
(74) *Attorney, Agent, or Firm* — Thomas | Horstemeyer, LLP

(57) ABSTRACT

The present disclosure provides a method for refining styrene by using falling film reboilers and heat pump technology to provide a heat source required by a separation column. According to the method, high-concentration gas-
(Continued)

phase ethylbenzene separated from a top of a low pressure ethylbenzene/styrene column is directly pressurized through a compressor, or a heat pump working medium is gasified using the high-concentration gas-phase ethylbenzene separated from the top of the low pressure ethylbenzene/styrene column, and the gasified heat pump working medium is pressurized. The directly pressurized high-concentration gas-phase ethylbenzene or the indirectly gasified and pressurized high-concentration gas-phase ethylbenzene is fed into the falling film reboiler with low heat transfer temperature difference requirement to serve as a heat source of a pre-separation column and/or a styrene product column in a styrene separation process.

9 Claims, 5 Drawing Sheets

(51) Int. Cl.
   *B01D 3/14* (2006.01)
   *B01D 5/00* (2006.01)
   *C07C 7/04* (2006.01)

(56) References Cited

U.S. PATENT DOCUMENTS

| | | | |
|---|---|---|---|
| 6,171,449 B1* | 1/2001 | Welch | B01D 3/146 |
| | | | 203/1 |
| 8,742,186 B2* | 6/2014 | Gartside | C07C 5/2506 |
| | | | 585/315 |
| 9,574,829 B2* | 2/2017 | Yang | B01D 3/007 |
| 9,902,667 B2* | 2/2018 | Welch | C07C 5/327 |
| 10,450,241 B2* | 10/2019 | Panditrao | C07C 2/66 |
| 2015/0336859 A1 | 11/2015 | Welch | |
| 2018/0079699 A1* | 3/2018 | Panditrao | C07C 7/04 |

FOREIGN PATENT DOCUMENTS

| | | |
|---|---|---|
| CN | 101602640 B | 12/2009 |
| CN | 105669353 A | 6/2016 |
| CN | 105669354 A | 6/2016 |
| CN | 105669354 B | 6/2016 |
| CN | 106631663 A | 5/2017 |
| CN | 113877227 A | 1/2022 |

OTHER PUBLICATIONS

Study on the Inhibitor in the Styrene Distillation Processing (65 pages).
International Search Report, PCT/CN2022/108063, mailed Oct. 25, 2022.
Sulzer Chemtech. (n.d.). Separation technology for the chemical process industry. https://www.sulzer.com/-/media/files/products/process-techology/processes-and-applications/brochures/separation_technology_for_the_chemical_process_industry.pdf.
Albert Meili et al. Heat Pumps for Distillation Columns Chemical Engineering Progress No. 6 New York Jun. 1990.
Xingang Li, Chengtian Cui, Hong Li, Xin Gao, Process synthesis and simulation-based optimization of ethylbenzene/ styrene separation using double-effect heat integration and self-heat recuperation technology: A techno-economic analysis, Separation and Purification Technology, vol. 228,2019, 115760,ISSN 1383-5866, https://doi.org/10.1016/j.seppur.2019.115760. (https://www.sciencedirect.com/science/article/pii/S1383586619316260).
Chengtian Cui, Xingang Li, Dongrong Guo, Jinsheng Sun, Towards energy efficient styrene distillation scheme: From grassroots design to retrofit, Energy, vol. 134,2017, pp. 193-205, ISSN 0360-5442, https://doi.org/10.1016/j.energy.2017.06.031.
Harold Gilman et al. Procede pour separer Pethylbenzene non transforme d'un courant gazeux Mar. 24, 1966.

* cited by examiner

METHOD FOR REFINING STYRENE BY USING COMBINED FALLING FILM REBOILERS AND HEAT PUMP TECHNOLOGY TO PROVIDE HEAT SOURCE OF SEPARATION COLUMN

CROSS REFERENCE TO RELATED APPLICATION

This patent application claims the benefit and priority of Chinese Patent Application No. 202111145258.7 filed with the China National Intellectual Property Administration on Sep. 28, 2021, the disclosure of which is incorporated by reference herein in its entirety as part of the present application.

TECHNICAL FIELD

The present disclosure belongs to the technical field of petrochemical engineering, and in particular, to method for refining styrene by using combined falling film reboilers and heat pump technology to provide heat source of separation column.

BACKGROUND ART

Styrene is the third largest polymer monomer next only to ethylene and propylene. In China, styrene is mainly used in the production of polystyrene and acrylonitrile-butadiene-styrene (ABS)/styrene-acrylonitrile (SAN) resin. Expandable polystyrene (EPS) accounts for about 38%, non-expandable polystyrene (general purpose polystyrene (GPPS)/high impact polystyrene (HIPS)) accounts for about 31%, ABS/SAN resin accounts for about 10%, unsaturated polyester resin (UPR) accounts for about 7%, and styrene butadiene rubber/styrene butadiene latex (SBR/SBL) accounts for about 7% of the total consumption. The rest of the total consumption are styrene based copolymers (styrene based thermoplastic elastomer, methacrylic acid butadiene styrene copolymer resin, styrene-divinylbenzene ion exchange resin, etc.).

At present, the mainstream methods for producing styrene include the catalytic dehydrogenation of ethylbenzene, the co-production of styrene and propylene oxide (namely, the propylene oxide/styrene monomer (PO/SM) process), the ethylbenzene dehydrogenation and selective oxidation process, and the recovery from pyrolysis gasoline by extractive distillation, etc., wherein the catalytic dehydrogenation of ethylbenzene and the co-production of styrene and propylene oxide (namely, the PO/SM process) are mainly used. The co-production of styrene and propylene oxide accounts for about 85% of the styrene production capacity. Although the co-production has a complex process flow and is cost-ineffective, it has developed rapidly in recent years because two important basic organic raw materials can be obtained at the same time through this process. By 2020, there are more than 40 major styrene producers in China, with the styrene production capacity exceeding 10 million tons/year.

Li Xueyun, in the master's thesis "Study on the Inhibitor in the Styrene Distillation Processing" of East China University of Science and Technology, reveals the relationship between the conversion rate of pure styrene polymerization and time at different temperatures without the addition of inhibitors through experiments. Through experimental analysis, it is found that the conversion rate of pure styrene polymerization increases with the temperature in the same reaction time, and the conversion rate of polymerization reaction increases with the time at the same temperature. In general, the conversion rate of polymerization reaction nearly doubles when the temperature increases by 10'.

In view of the problems, those skilled in the art propose different improved methods. For example, the distillation process for separating ethylbenzene/styrene from a dehydrogenated liquid mixture by a high pressure column and a low pressure column coupled to the high pressure column is the most advanced energy-saving process for separating ethylbenzene/styrene from the dehydrogenated liquid mixture.

The Chinese patent CN1163289C discloses a series reboiling method for an ethylbenzene/styrene column. The patent requires providing a high pressure column and a low pressure column thermally coupled to the high pressure column, and steam at the top of the high pressure column is used as a heat source of a reboiler of the low pressure column. The high pressure column and the low pressure column have the same feeding source, with the same composition and temperature, and the products separated by the kettles of the high pressure column and low pressure column have the same composition and serve as the fed material of another column. However, this solution only achieves the thermal coupling of the high and low pressure ethylbenzene/styrene columns themselves, and the thermal energy utilization rate is still at a low level.

The Chinese patent CN101602640B discloses a method for separating ethylbenzene/styrene that is energy-saving, which divides the ethylbenzene/styrene separation column into two columns from a single column for operation. The steam at the top of the ethylbenzene/styrene separation column A is partially or wholly introduced into the compressor, and the compressed process gas is used as the heat source of the reboiler of the ethylbenzene/styrene separation column B. The patent additionally uses compressor pressurization to ensure the thermal coupling effect between high and low pressure columns. This method involves high energy consumption and poor economy, and can only conduct heat pump cycle between high and low pressure ethylbenzene/styrene columns. Energy utilization needs to be further improved.

The Chinese patent CN105669354B discloses a method for separating ethylbenzene dehydrogenation reaction products, which separates a dehydrogenated liquid mixture through a crude styrene separation column. The gas phase containing benzene, toluene, and ethylbenzene at the top of the column is compressed as the heat source of the reboilers for separating benzene and toluene at the top of the column, and ethylbenzene at the kettle, and as the heat source of the reboiler of the styrene product column. In the present disclosure, the separation of ethylbenzene/styrene is realized by only one column, and the compressor inlet gas contains almost all benzene and toluene brought in by the dehydrogenated liquid mixture, so the compressor inlet pressure and temperature are low, which will lead to high consumption and poor economy.

To sum up, the existing processes for refining styrene still involve the problems of insufficient energy utilization, high energy consumption, and poor economy, so it is necessary to further explore and improve the existing processes.

SUMMARY

An objective of the present disclosure is to solve the shortcomings of the prior art, and discloses a method for refining styrene by using falling film reboilers and heat pump technology to provide a heat source of a separation column. According to the method, based on an energy-saving technology of coupled high and low pressure ethylbenzene/styrene separation columns, through an open or closed heat pump cycle, combined with the arrangement and utilization of the falling film reboilers, energy consumption in the styrene separation process is further greatly reduced, an energy utilization rate is improved, and the economic efficiency of the device is improved.

A technical solution of the present disclosure is as follows: a method for refining styrene by using falling film reboilers and heat pump technology to provide a heat source of a separation column is provided. A refining route from upstream to downstream includes a pre-separation column, a high pressure ethylbenzene/styrene column, a low pressure ethylbenzene/styrene column, and a styrene product column, and a total flow at a kettle of the pre-separation column from a bottom of the pre-separation column is divided into two streams in which one of the streams is fed into the high pressure ethylbenzene/styrene column and other is fed into the low pressure ethylbenzene/styrene column. Ethylbenzene flows separated from tops of the high pressure ethylbenzene/styrene column and the low pressure ethylbenzene/styrene column are fed into a ethylbenzene dehydrogenation unit as a raw material, and flows from corresponding kettles are fed into the styrene product column. Tar with styrene not completely removed in a column kettle of the styrene product column is fed into a styrene recovery system. A mixture of benzene and toluene separated from a top of the pre-separation column is continuously separated to obtain benzene returned to an ethylbenzene unit as a raw material and toluene as a by-product. The low pressure ethylbenzene/styrene column is connected to a reboiler of the low pressure ethylbenzene/styrene column, a product flow of the low pressure ethylbenzene % styrene column obtained from a bottom of the low pressure ethylbenzene/styrene column is fed into the styrene product column, and a circulation flow of the low pressure ethylbenzene/styrene column flows through the reboiler of the low pressure ethylbenzene/styrene column and is partially gasified through heating by a gas phase flow distilled from the top of the high pressure ethylbenzene/styrene column and then returned to the bottom of the low pressure ethylbenzene/styrene column. The high pressure ethylbenzene/styrene column is connected to a reboiler of the high pressure ethylbenzene/styrene column, a product flow of the high pressure ethylbenzene/styrene column from a bottom of the high pressure ethylbenzene/styrene column is fed into the styrene product column, and a distillate from the top of the high pressure ethylbenzene/styrene column is fed into the reboiler of the low pressure ethylbenzene/styrene column.

An open heat pump cycle or a closed heat pump cycle is set at the top of the low pressure ethylbenzene/styrene column.

The pre-separation column is provided with a reboiler using a gas phase medium fed by an open or closed heat pump as a heat source.

The styrene product column is provided with a reboiler using a gas phase medium fed by the open or closed heat pump as a heat source.

The open heat pump cycle is as follows: the top of the low pressure ethylbenzene/styrene column is connected to an ethylbenzene heat pump compressor, and part of a gas phase flow from the top of the low pressure ethylbenzene/styrene column is compressed by the ethylbenzene heat pump compressor and then configured as a heat source of the pre-separation column and/or the styrene product column. Another part of the gas phase flow that is unpressurized is fed into a condenser of the low pressure ethylbenzene/styrene column for condensation, condensate and a flow condensed by the reboiler of the pre-separation column and/or the reboiler of the styrene product column are collected together and pressurized as a total condensate flow, part of the total condensate flow is configured as reflux of the low pressure ethylbenzene/styrene column, and a remaining part of the total condensate is sent to the ethylbenzene dehydrogenation unit for recycling as a extracted flow.

The closed heat pump cycle is as follows: the gas phase flow at the top of the low pressure ethylbenzene/styrene column is fed into a heat pump working medium evaporator of the low pressure ethylbenzene/styrene column as a heat source for evaporation of a heat pump working medium, and an uncondensed flow is continuously fed into an aftercondenser of the low pressure ethylbenzene/styrene column for condensation. The evaporated heat pump working medium is pressurized by a working medium heat pump compressor and fed into the reboiler of the pre-separation column and/or the reboiler of the styrene product column as a heat source, and a heat pump working medium condensed by the reboiler of the pre-separation column and/or the reboiler of the styrene product column is recycled back to the heat pump working medium evaporator of the low pressure ethylbenzene/styrene column.

Furthermore, the ethylbenzene heat pump compressor and the working medium heat pump compressor can be jointly arranged, and provide heat for the reboiler of the pre-separation column and the reboiler of the styrene product column simultaneously. Or alternatively, compressors with different outlet pressures are arranged independently according to different condensing pressures required by heat source sides of the reboiler of the pre-separation column and the reboiler of the styrene product column.

Furthermore, the reboiler on the pre-separation column, the reboiler on the styrene product column, and the low pressure ethylbenzene/styrene reboiler are all falling film reboilers.

Furthermore, both the falling film reboiler of the pre-separation column and the falling film reboiler of the styrene product column are equipped with a circulating pump to establish a circulation flow required by the falling film reboilers.

Furthermore, the top of the pre-separation column is connected to a condenser of the pre-separation column, a top of the styrene product column is connected to a condenser of the styrene product column, and both the condenser of the pre-separation column and the condenser of the styrene product column utilize circulating water as a cold source.

Furthermore, in the open heat pump cycle, the circulating water for the condenser of the styrene product column and the condenser of the pre-separation column is connected in series with circulating water for the condenser of the low pressure ethylbenzene/styrene column, and both the condenser of the styrene product column and the condenser of the pre-separation column are placed in a front portion of a circulating water flow path.

Furthermore, in the closed heat pump cycle, the circulating water for the condenser of the styrene product column and the condenser of the pre-separation column is connected in series with circulating water for the aftercondenser of the low pressure ethylbenzene/styrene column, and both the condenser of the styrene product column and the condenser of the pre-separation column are placed in a front portion of a circulating water flow path.

Furthermore, the low pressure ethylbenzene/styrene column has an operating pressure of 7-17 KPaA.

Furthermore, the pre-separation column has an operating pressure of 12-19 KPaA.

Furthermore, the styrene product column has an operating pressure of 2-5 KPaA.

The present disclosure has the following beneficial effects:

1. According to the method, based on an existing energy-saving technology of coupled high and low pressure ethylbenzene/styrene separation columns, by further using the heat pump technology combined with the use of the falling film reboilers, the energy at the top of low pressure ethylbenzene/styrene column is used as the heat source of the pre-separation column and/or the styrene product column. This design can make full use of the heat transfer temperature difference, energy consumption in the styrene separation process is further greatly reduced, costs can be recovered within a relatively short period of time after the production process is correspondingly improved and put into production, and long-term economic benefits are remarkable.

2. The present disclosure can realize the reuse of the energy at the top of the low pressure ethylbenzene/styrene column by combining the open heat pump technology with the falling film reboilers. High-concentration gas-phase ethylbenzene separated from the top of the low pressure ethylbenzene/styrene column is directly pressurized through a compressor. A directly pressurized high-concentration gas-phase ethylbenzene is fed into the falling film reboiler with low heat transfer temperature difference requirement to serve as the heat source of the pre-separation column in the styrene separation process or the heat source of the styrene product column, so as to save energy and operating costs.

3. The present disclosure can realize the reuse of the energy at the top of the low pressure ethylbenzene/styrene column by combining the closed heat pump technology with the falling film reboilers. A heat pump working medium is gasified by high-concentration gas-phase ethylbenzene separated from the top of the low pressure ethylbenzene/styrene column, and the gasified heat pump working medium is pressurized. The indirectly gasified and pressurized high-concentration gas-phase ethylbenzene is fed into the falling film reboiler with low heat transfer temperature difference requirement to serve as the heat source of the pre-separation column in the styrene separation process or the heat source of the styrene product column, so as to save energy and operating costs.

4. On the basis of selecting and utilizing the heat pump technology and the falling film reboilers, the present disclosure uses the available gas phase at the top of the circulating water condensing column as the bottleneck of column pressure design of the pre-separation column and the styrene product column to minimize the operating pressure of the pre-separation column and/or styrene product column heated and the pressure difference between the top and bottom of the pre-separation column and/or styrene product column, so as to reduce temperature at the kettle and energy consumption of the compressor.

5. The present disclosure enables the heat input from the high pressure ethylbenzene/styrene column kettle to be used for three times, and has the advantage of reducing the power of the heat pump compressor by increasing the operating pressure at the top of the low pressure ethylbenzene/styrene separation column and reducing the pressure of the pre-separation column and/or the styrene product column.

REFERENCE NUMERALS

Figure 1:
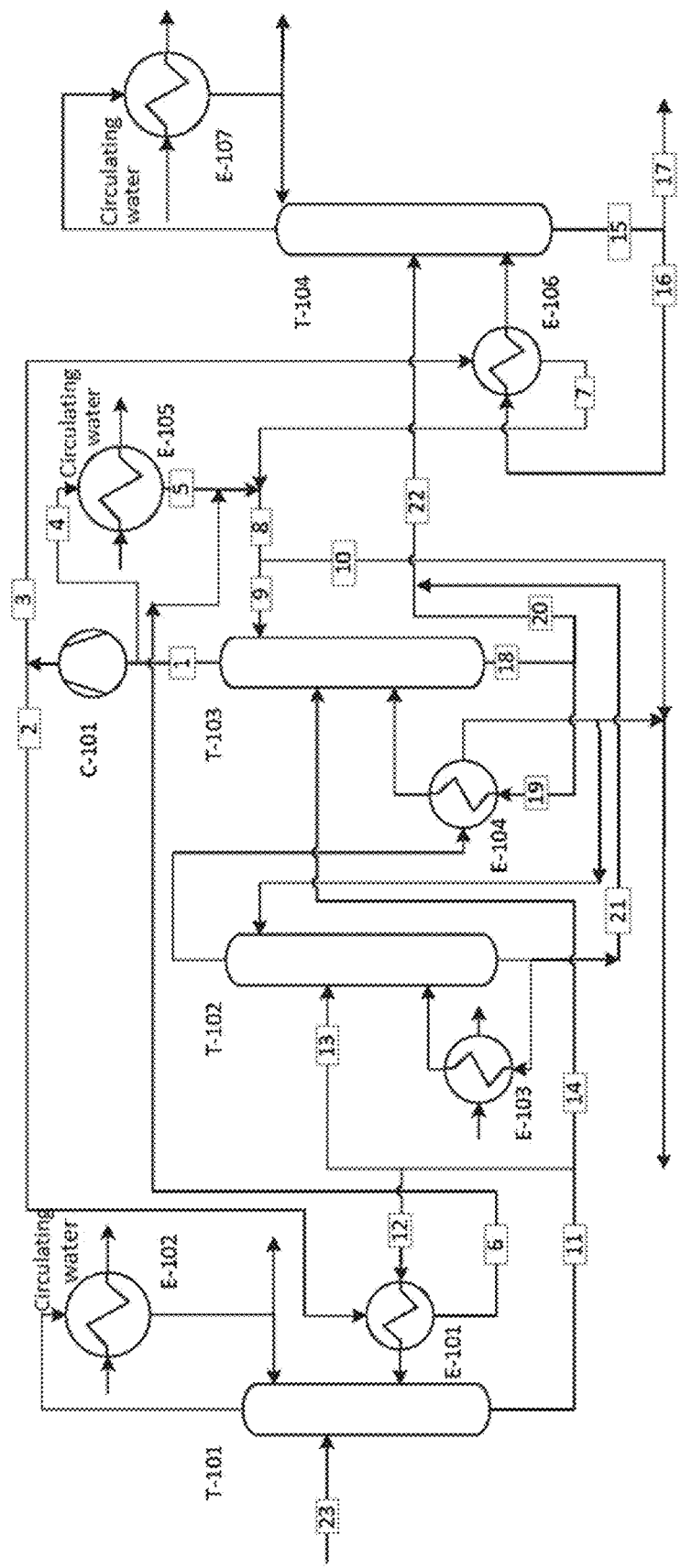
FIG. 1 is a route diagram of a styrene refining process by using combined open heat pump technology and falling film reboilers to provide a heat source of a pre-separation column and a styrene product column disclosed in Example I.

T-101: pre-separation column, T-102: high pressure ethylbenzene/styrene column, T-103: low pressure ethylbenzene/styrene column, T-104: styrene product column, E-101: falling film reboiler of pre-separation column, E-102: condenser of pre-separation column, E-103: reboiler of high pressure ethylbenzene/styrene column, E-104: falling film reboiler of low pressure ethylbenzene/styrene column, E-105: condenser of low pressure ethylbenzene/styrene column, E-106: falling film reboiler of styrene product column, E-107: condenser of styrene product column, E-108: heat pump working medium evaporator of low pressure ethylbenzene/styrene column, E-109: aftercondenser of low pressure ethylbenzene/styrene column, C-101: ethylbenzene heat pump compressor, and C-102: working medium heat pump compressor;

1: gas phase flow at top of low pressure ethylbenzene/styrene column, 2: first gas phase flow, 3: second gas phase flow, 4: unpressurized gas phase flow, 5: condensate, 6: first condensed flow, 7: second condensed flow, 8: total condensate flow, 9: reflux, 10: total extracted flow, 11: total flow at kettle of pre-separation column, 12: circulation flow of pre-separation column, 13: feed of high pressure ethylbenzene/styrene column, 14: feed of low pressure ethylbenzene/styrene column, 15: total flow, 16: circulation flow of styrene product column, 17: feed of styrene recovery column, 18: effluent of low pressure ethylbenzene/styrene column, 19: circulation flow of low pressure ethylbenzene/styrene column, 20: product flow of low pressure ethylbenzene/styrene column, 21: product flow of high pressure ethylbenzene/styrene column, 22: total feed of styrene product column, and 23: dehydrogenated liquid; and

2': first heat pump working medium gas phase flow, 3': second heat pump working medium gas phase flow, 4': evaporated heat pump working medium, 5': total condensed heat pump working medium, 6': first condensed heat pump working medium, and 7': second condensed heat pump working medium.

Note: In order to simplify the process, pumps and reflux tanks required for realizing the process in the above figures are not shown.

DETAILED DESCRIPTION OF THE EMBODIMENTS

The following examples further illustrate the content of the present disclosure, but should not be understood as limiting the present disclosure. Modifications or substitutions made to methods, steps or conditions of the present disclosure without departing from the essence of the present disclosure fall within the scope of the present disclosure.

The dehydrogenated liquid mixture contains water, benzene, toluene, ethylbenzene, styrene, and tar. At the top of a pre-separation column, benzene, toluene and trace water in the dehydrogenated liquid mixture are separated, and ethylbenzene, styrene, and tar are separated at the column kettle, so the temperature difference between the top and bottom of the pre-separation column is large. Taking the pressure drop at the top of the pre-separation column as 20 KPaA as an example, the typical temperature at the top of the pre-separation column is 55.18° C., the typical temperature at the bottom of the pre-separation column is 91.9° C., and the temperature difference between the top and bottom of the pre-separation column is 36.72° C. Obviously, it is not economical to provide a heat pump that uses the gas phase at the top of the pre-separation column as a heat source to heat the reboiler.

When the pressure drop at the top of a styrene product column is 6 KPaA, the temperature of gas phase styrene at the top of the styrene product column is 63.56° C., and the corresponding pressure at the column kettle of the styrene product column is 9 KPaA, and the column kettle liquid has a styrene content of 70%, the reboiler has an outlet temperature of 78.87° C. The temperature difference between the top and bottom of the styrene product column is small, so a heat pump that uses the gas phase at the top of the styrene product column as a heat source to heat the column kettle of the styrene product column can be provided. However, compared with the heat pump process using gas phase at the top of a low pressure ethylbenzene/styrene separation column, which has a higher temperature than the top of the styrene product column, as a heat source to heat the reboiler of the styrene product column, the economy is obviously weak.

In the styrene device designed and operated by Changzhou Ruihua Chemical Engineering Technology Co., Ltd., steam with an extremely low pressure of 0.04 MPaG has been used as heat sources for the reboilers of the pre-separation column and the styrene product column, which has mature experience in reducing the temperature at the column kettles of the pre-separation column and the styrene product column and ensuring the stable operation of the styrene separation process under high vacuum. On the basis of the existing devices, tests that reducing the pressure at the top and the column kettles of the pre-separation column and styrene product column have been conducted under low load conditions, and further simulation calculations have been conducted to determine the feasibility and economy of the pre-separation column and the styrene product column receiving heat from an open or closed heat pump at the top of the low pressure ethylbenzene/styrene column through the falling film reboiler as a heat source.

Example I: A Method for Refining Styrene by Using Falling Film Reboilers and Open Heat Pump Technology to Provide a Heat Source Required by a Separation Column In order to further reduce the operation energy consumption and improve the economy of the ethylbenzene/styrene separation device, the present disclosure added a heat pump circulation device to the existing distillation processing device for separating ethylbenzene/styrene from a dehydrogenated liquid mixture with a high pressure column and a low pressure column coupled to the high pressure column.

The heat pump cycle, namely the reverse Carnot cycle, was as follows: a small amount of high-grade energy was applied to the low temperature heat of the fluid at the top of the recovery column through the compressor to raise its temperature level, which could be used as the heat source at the bottom of the column, so as to save energy and operating costs.

The heat pump technology could be divided into open heat pump technology and a closed heat pump technology. The open heat pump technology was a technology that uses a compressor to directly compress high-concentration gas-phase ethylbenzene at the top of the low pressure ethylbenzene/styrene column as the heat sources of reboilers of the pre-separation column and the styrene product column.

This example focused on a method of refining styrene by using open heat pump technology and falling film reboilers to provide heat sources required by the pre-separation column and the styrene product column. The specific process route is shown in FIG. 1.

The refining process route of styrene from upstream to downstream was provided with four key columns in sequence: a pre-separation column T-101, a high pressure ethylbenzene/styrene column T-102, a low pressure ethylbenzene/styrene column T-103, and a styrene product column T-104. The pre-separation column T-101 separates benzene and toluene in the dehydrogenated liquid mixture from the top thereof and separates ethylbenzene, styrene, and tar in the dehydrogenated liquid mixture from the column kettle thereof. The high pressure ethylbenzene/styrene column T-102 and the low pressure ethylbenzene/styrene column T-103 separate the ethylbenzene from the tops thereof, separate the styrene and the tar from the column kettle thereof, had the same function, and were thermally coupled. The styrene product column T-104 separates the styrene from the top thereof, and separates all the tar along with a small amount of the styrene entrained from the column kettle thereof.

The top of the pre-separation column T-101 was connected to a condenser of the pre-separation column E-102. The condensed liquid phase was collected through a reflux tank and pressurized to be used as reflux and extract. A total flow at the column kettle of the pre-separation column 11 from the bottom of pre-separation column T-101 is divided into two streams (namely, feed of the high pressure ethylbenzene/styrene column 13 and feed of the low pressure ethylbenzene/styrene column 14) one of which is fed into the high pressure ethylbenzene/styrene column T-102 and the other is fed into the low pressure ethylbenzene/styrene column T-103. The lower area of the pre-separation column T-101 is connected to a falling film reboiler of the pre-separation column E-101.

The styrene product column T-104 is connected to a falling film reboiler of the styrene product column E-106. A total flow 15 from the bottom of the styrene product column T-104 is divided into feed of a styrene recovery column 17 and a circulation flow of the styrene product column 16. The circulation flow of the styrene product column 16 flows through the falling film reboiler of the styrene product column E-106, and the heated circulation flow of the styrene product column 16 is output and returned to the lower area of the styrene product column T-104. The top of the styrene product column is connected to a condenser of the styrene product column E-107. The condensed liquid phase is collected through a reflux tank and pressurized to be used as a reflux and a extracted product styrene.

The high pressure ethylbenzene/styrene column T-102 is connected to a reboiler of the high pressure ethylbenzene/styrene column E-103. The product flow of the high pressure column 21, which mainly contains high-concentration styrene monomer, from the bottom of the high pressure ethylbenzene/styrene column T-102 is fed into the styrene product column T-104. A gas phase distillate at the top of the high pressure ethylbenzene/styrene column mainly contains ethylbenzene. The gas phase distillate at the top of the high pressure ethylbenzene/styrene column is used for the heat supply of the falling film reboiler of the low pressure ethylbenzene/styrene column. The gas phase distillate is condensed after heat transfer to the falling film reboiler of the low pressure ethylbenzene/styrene column. One part of the condensed gas phase distillate is used as a reflux, and the other part of the condensed gas phase distillate is extracted as circulating ethylbenzene and fed into a dehydrogenation unit for recycling.

The low pressure ethylbenzene/styrene column T-103 is connected to a falling film reboiler of the low pressure ethylbenzene/styrene column E-104. Effluent of the low pressure ethylbenzene/styrene column 18, which mainly contains high-concentration styrene monomer, from the bottom of the low pressure ethylbenzene/styrene column T-103 is divided into a product flow of the ethylbenzene/styrene low pressure column 20 and a circulation flow of the low pressure ethylbenzene/styrene column 19. The product flow of the ethylbenzene/styrene low pressure column 20 is fed into the styrene product column T-104, and the circulation flow of the low pressure ethylbenzene/styrene column 19 flows through the falling film reboiler of the low pressure ethylbenzene/styrene column E-104, and is partially gasified through heating by the gas phase flow distillate at the top of the high pressure ethylbenzene/styrene column and returned to the bottom of the low pressure ethylbenzene/styrene column T-103.

The gas phase flow at the top of the low pressure ethylbenzene/styrene column 1 is divided into two gas phase flows. One gas phase flow can be divided into a first gas phase flow 2 and a second gas phase flow 3 after being pressurized by an ethylbenzene heat pump compressor C-101. The first gas phase flow 2 is fed into the falling film reboiler of the pre-separation column E-101 as the heat source of the pre-separation column T-101, and the second gas phase flow 3 is fed into the falling film reboiler of the styrene product column E-106 as the heat source of the styrene product column T-104. The other unpressurized gas phase flow 4 is fed into a condenser of the low pressure ethylbenzene/styrene column E-105 for condensation, and condensate 5 and a first condensed flow 6 condensed by the falling film reboiler of the pre-separation column E-101 and a second condensed flow 7 condensed by the falling film reboiler of the styrene product column E-106 are collected together and pressurized as a total condensate flow 8. The total condensate flow 8 is transported to an ethylbenzene dehydrogenation unit for recycling as the reflux 9 of the low pressure ethylbenzene/styrene column T-103 or as the total extracted flow 10. The condenser of the low pressure ethylbenzene/styrene column E-105 played an auxiliary role in adjusting the condensing load during startup and shutdown or under fluctuating operating conditions.

The falling film reboiler of the pre-separation column E-101 needs to be equipped with a circulating pump to establish the circulation flow of the pre-separation column 12. The falling film reboiler of the styrene product column E-106 needs to be equipped with a circulating pump to establish the circulation flow of the styrene product column 16.

The condenser of the pre-separation column E-102, the condenser of the low pressure ethylbenzene/styrene column E-105, and the condenser of the styrene product column E-107 in this example still use circulating water as a cold source, just like the coupled high and low pressure sequential separation process mentioned above. The circulating water for the condenser of the styrene product column E-107 and the condenser of the pre-separation column E-102 are connected in series with circulating water for the condenser of the low pressure ethylbenzene/styrene column E-105, and both the condenser of the styrene product column E-107 and the condenser of the pre-separation column E-102 are placed in a front portion of a circulating water flow path, so as to reduce circulating water consumption.

The specific working process is as follows.

(1) The dehydrogenated liquid 23 first is fed into the pre-separation column T-101, which is a highly efficient packed distillation column operated under negative pressure. The pre-separation column T-101 is used to separate light components such as toluene and benzene in the dehydrogenated liquid 23 with a boiling point lower than that of ethylbenzene from the top of the pre-separation column T-101, and the total flow at the kettle of the pre-separation column 11 (mainly a mixture containing ethylbenzene, styrene, and tar) is obtained at the bottom of the pre-separation column. Then, the total flow at the kettle of the pre-separation column 11 is divided into two streams (namely, the feed of the high pressure ethylbenzene/styrene column 13 and the feed of the low pressure ethylbenzene/styrene column 14), which were respectively fed into the high pressure ethylbenzene/styrene column T-102 and the low pressure ethylbenzene/styrene column T-103 for further treatment.

(2) The main equipment of ethylbenzene recovery and crude styrene ethylene separation system is two high and low pressure packed columns T-102/T-103 which are coupled and have high efficiency and low pressure drop. The ethylbenzene distilled from the tops of the high and low pressure packed columns is recycled back to the dehydrogenation reaction system as a part of the feed ethylbenzene of the reactor. The crude styrene obtained at the bottoms of the high and low pressure packed columns, that is, the product flow of the low pressure column 20 and the product flow of the high pressure column 21, are combined into the total feed of the styrene product column 22 and fed into the styrene product column T-104 for separation to obtain qualified styrene products.

(3) The gas phase flow at the top of the pre-separation column 1 is divided into two gas phase flows. One of the gas phase flows is divided into a first gas phase flow 2 and a second gas phase flow 3 after being pressurized by the ethylbenzene heat pump compressor C-101. The first gas phase flow 2 is fed into the falling film reboiler of the pre-separation column E-101 as the heat source of the pre-separation column, and the second gas phase flow 3 is fed into the falling film reboiler of the styrene product column E-106 as the heat source of the styrene product column T-104. The other gas phase flow 4 that is unpressurized is fed into the condenser of the low pressure ethylbenzene/styrene column E-105 for condensation.

(4) The main function of the styrene product column T-104 is to produce styrene products at the top thereof and tar with high concentration of styrene at the column kettle thereof to form the feed of the styrene recovery column 17, which is sent to the styrene recovery system to recover styrene, and tar with a styrene content less than 6% is extracted in the styrene recovery system.

Figure 2:
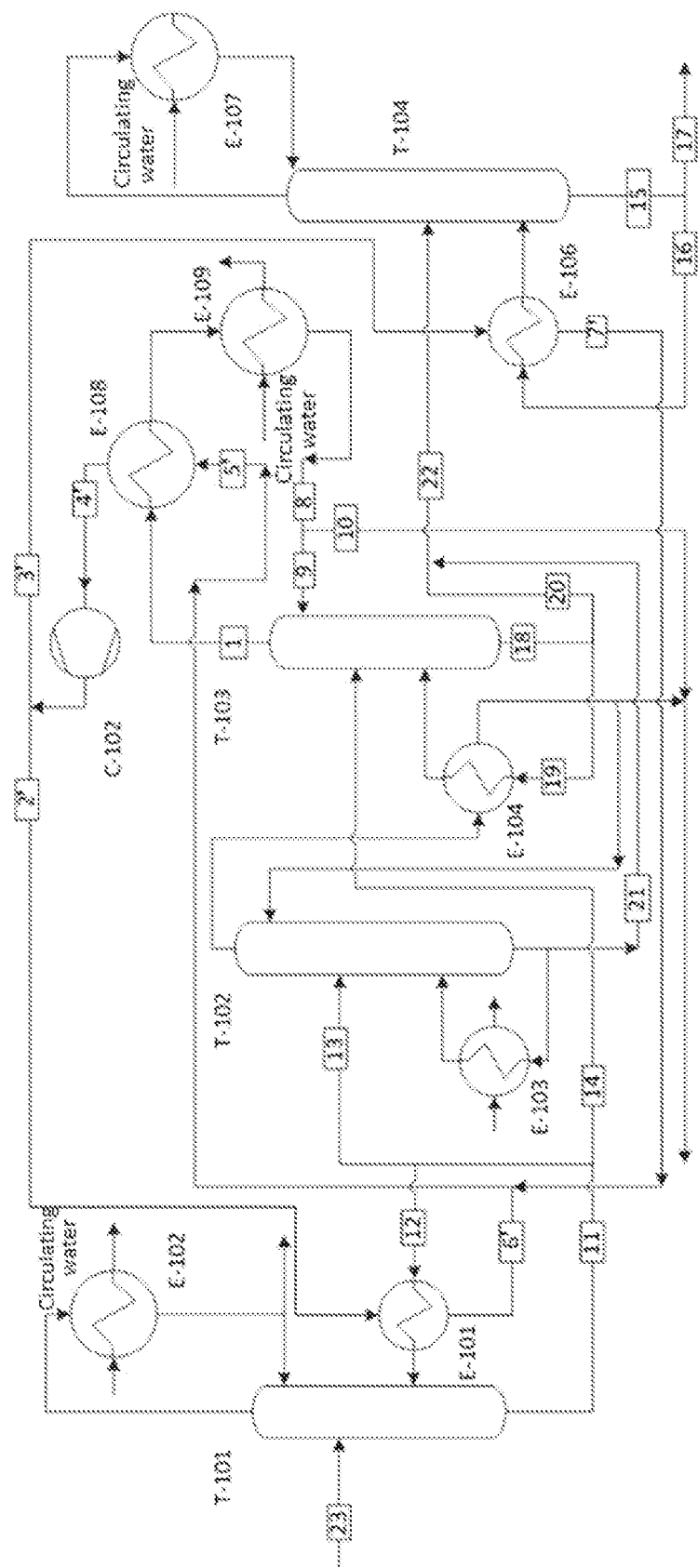
FIG. 2 is a route diagram of a styrene refining process by using combined closed heat pump technology and falling film reboilers to provide a heat source of a pre-separation column and a styrene product column disclosed in Example II.

Example II: A Method for Refining Styrene by Using Falling Film Reboilers and Closed Heat Pump Technology to Provide a Heat Source of a Separation Column This example focused on a method for refining styrene by using closed heat pump technology and reboilers to provide a heat source of the separation column. The specific process route is shown in FIG. 2.

The difference from the open heat pump technology was as follows.

The gas phase flow at the top of the low pressure ethylbenzene/styrene column 1 is fed into a heat pump working medium evaporator of the low pressure ethylbenzene/styrene column E-108, and the uncondensed gas phase flow is continuously fed into the aftercondenser of the low pressure ethylbenzene/styrene column E-109 for condensation. The evaporated heat pump working medium 4' is pressurized by a working medium heat pump compressor C-102 and divided into a first heat pump working medium gas phase flow 2' and a second heat pump working medium gas phase flow 3'. The two gas phase flows are fed into the reboiler of the pre-separation column E-101 and/or the reboiler of the styrene product column E-106 respectively as a heat source. A first condensed heat pump working medium 6' and a second condensed heat pump working medium 7' condensed in E-101/106 are combined into a total condensed heat pump working medium 5', and recycled back to the heat pump working medium evaporator of the low pressure ethylbenzene/styrene column E-108 for continuous gasification for recycling.

The falling film reboiler of the pre-separation column E-101 needs to be equipped with a circulating pump to establish the circulation flow of the pre-separation column 12 required by the falling film reboiler. The falling film reboiler of the styrene product column E-106 needs to be equipped with a circulating pump to establish the circulation flow of the styrene product column 16 required by the falling film reboiler.

During Specific Work:

The closed heat pump gasifies the heat pump working medium using high-concentration gas-phase ethylbenzene separated from the top of the low pressure ethylbenzene/styrene column T-103, and the gasified heat pump working medium is pressurized. The indirectly gasified and pressurized heat pump working medium is fed into the falling film reboiler with low heat transfer temperature difference requirement to serve as the heat source of the pre-separation column T-101 or the styrene product column T-104 in the styrene separation process.

The closed heat pump working medium needs to be a medium with a pressure suitable for selection and low power of the compressor after being evaporated by the gas phase flow at the top of the low pressure ethylbenzene/styrene column, such as n-butane, isobutane, butene, pentane, cyclopentane, benzene, and methanol, etc.

The condenser of the pre-separation column E-102, the aftercondenser of the low pressure ethylbenzene/styrene column E-109, and the condenser of the styrene product column E-107 in this example still uses circulating water as a cold source, just like the distillation device for separating ethylbenzene/styrene with high pressure column and low pressure column coupled to the high pressure column mentioned above. The circulating water used for the condenser of the styrene product column E-107 and the condenser of the pre-separation column E-102 are connected in series with circulating water used for the aftercondenser of the low pressure ethylbenzene/styrene column E-109, and both the condenser of the styrene product column E-107 and the condenser of the pre-separation column E-102 are placed in a front portion of a circulating water flow path, so as to increase the heat transfer temperature difference between E-102 and E-107 and reduce circulating water consumption.

The reboiler of the pre-separation column, the reboiler of the styrene product column, and the low pressure ethylbenzene/styrene reboiler used in the above examples and the following application examples are all falling film reboilers. The reason for choosing the falling film reboiler is as follows: the falling film reboiler is one kind of reboiler, in addition to the kettle reboiler, the horizontal thermosyphon reboiler, the vertical thermosyphon reboiler, the forced circulation reboiler, etc. The falling film reboiler needs to be additionally equipped with a liquid phase circulating pump and a liquid phase distribution device, such as a distribution head and a liquid phase distribution disk, etc. The liquid phase is pulled into a film along the wall of a heat exchange tube through the distribution device, and the gas phase is evaporated along the film. Other types of reboilers, such as the thermosyphon reboiler, do not need to be provided with additional circulating pumps which relied on the density difference of their own liquid after heating to circulate. Due to the circulating pumps, the installation height of the falling film reboiler relative to the column body is generally not specified, but the installation height of the thermosyphon reboiler relative to the column kettle and the gas phase and liquid phase inlets and outlets need to be specially determined according to operating conditions thereof and material properties. Generally speaking, the falling film reboiler is more suitable for treatment of materials with high vacuum, strong heat sensitivity and high viscosity than the thermosyphon reboiler. The heat transfer temperature difference between the tube side and the shell side of the falling film reboiler can be reduced, and the heat exchange efficiency is high.

For the styrene product column with a high tar content in the column kettle, except that the pressure of the column kettle of the styrene product column affected the heat exchange effect of the reboiler, the tar concentration in the column kettle and the gasification rate of the reboiler had more influence on the heat exchange effect of the reboiler. Therefore, the falling film reboiler needed to be selected to reduce the heat transfer temperature difference between the tube side and the shell side of the falling film reboiler by increasing the styrene content in the products of the kettle of the styrene product column and reducing the gasification rate of the falling film reboiler.

Application Example I

A styrene separation unit for producing styrene by dehydrogenation of 500,000 tons of ethylbenzene is taken as an example. The top of the low pressure ethylbenzene/styrene column T-103 contains high-concentration gas-phase ethylbenzene, which is pressurized by the ethylbenzene heat pump compressor C-101, and only provides a heat source for the falling film reboiler of the styrene product column E-106.

Figure 3:
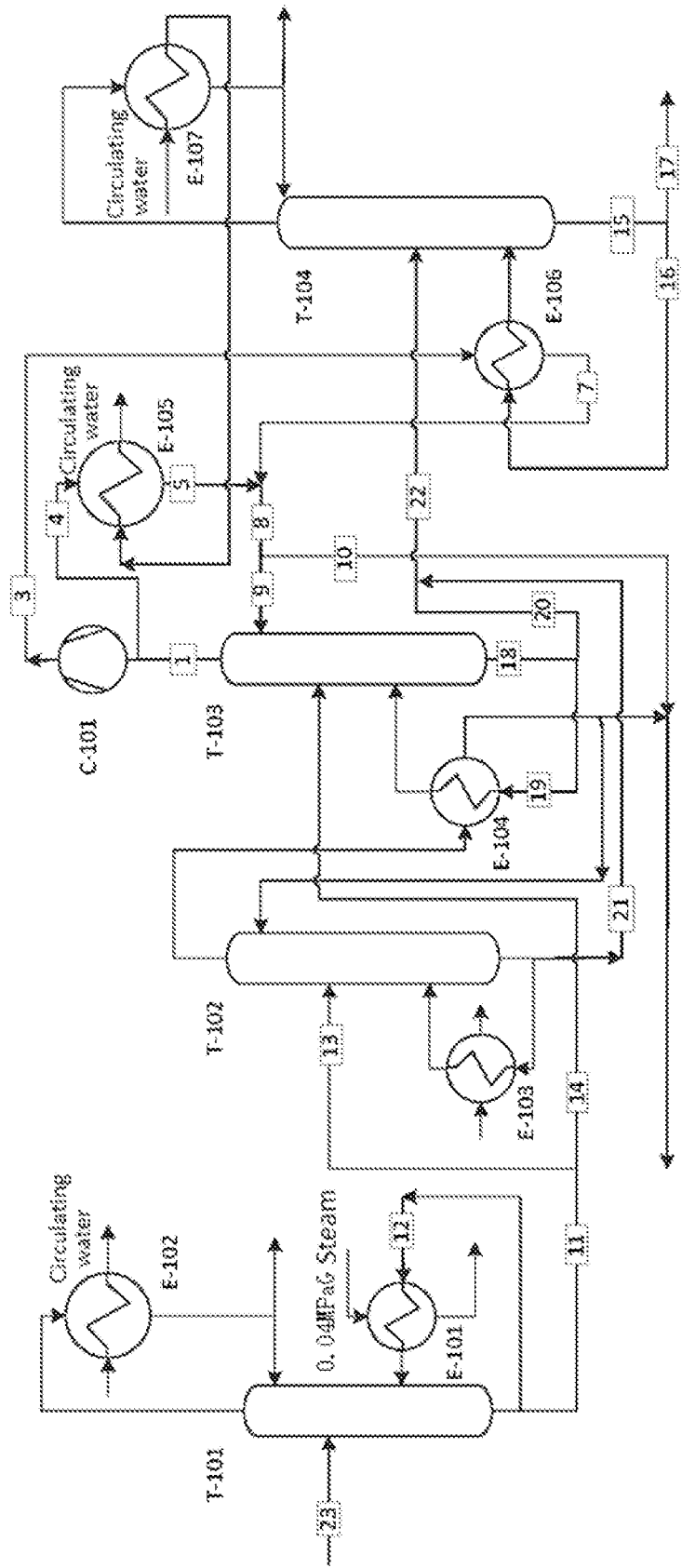
FIG. 3 is a route diagram of a styrene refining process by using combined open heat pump technology and falling film reboilers to provide a heat source of a styrene product column disclosed in Application Example I.

The specific process route is shown in FIG. 3.

a) The pressure is 10 KPaA and the temperature is 67.04° C. at the top of the low pressure ethylbenzene/styrene column T-103, and the high-concentration gas-phase ethylbenzene at the top of the low pressure ethylbenzene/styrene column is fed into the falling film reboiler of the styrene product column E-106 at a flow rate of 78.86 t/h after being pressurized by the ethylbenzene heat pump compressor C-101;

b) The pressure is 2.5 KPaA and the temperature is 45.45° C. at the top of the styrene product column T-104, the pressure at the column kettle is 5.6 KPaA, and the outlet temperature of the falling film reboiler of the styrene product column is 67.50.

c) Inlet conditions of the ethylbenzene heat pump compressor C-101: a pressure of 10 KPaA, a temperature of 67.04° C., and a flow rate of 78.86 t/h. Outlet conditions of the ethylbenzene heat pump compressor C-101: a pressure of 18 KPaA. The shaft power is 462.4 kW (efficiency of the ethylbenzene heat pump compressor is calculated as 75%). If the axial flow fan of Shaanxi Blower (group) Co., LTD. is selected, the model is ED160-2+2, the power is 539 (the maximum outlet pressure could reach 25 KPaA), and the rotate speed is 1,485.

d) The heat exchanger of the condenser of the styrene product column E-107 is of a BXM type, which is a through flow heat exchanger with a diameter of 4,000 mm, a length of 7,000 mm, a heat exchange area of 3,008 $m^2$, and a weight of 101.8 t. The styrene gas at the shell side gas is condensed by the circulating water at the tube side, the pressure drop at the shell side is 0.4 KPa, and the uncondensed gas-phase styrene at the outlet of the heat exchanger has a mass flow of 725 Kg/h.

e) The circulating water used for the condenser of the styrene product column E-107 is connected in series with the circulating water used for the condenser of the low pressure ethylbenzene/styrene column E-105, and the condenser of the styrene product column E-107 is placed in a front portion of the circulating water flow path, so as to increase the heat transfer temperature difference of the condenser of the low pressure ethylbenzene/styrene column E-105.

f) A heat load required by the falling film reboiler of the styrene product column E-106 is 8,059 kW. The falling film heat exchanger which is of a BEM type has a diameter of 3.80 mm, a length of 8,500 mm, a heat exchange area of 3,616 $m^2$, and a total volume of 129.5 t. The temperature difference is 7.2° C., the temperature at the shell side is 75.73-82.18° C., the temperature at the tube side is 67.5-70.66° C., the uncondensed gas volume at the shell side outlet has a mass flow of 1,563 Kg/h, and the gasification rate is 7%.

g) Circulating pump supporting for the falling film reboiler of the styrene product column has a design flow of 1,118 $m^2$/h (115% margin), a head of 36 m, and shaft power of 132 kW.

h) The styrene product column T-104 has a diameter of 5,000 mm, the column shell has a weight of 103.8 t, and the packing volume is 353 $m^3$.

Comparative Example I

This comparative example is mainly compared with Application Example I:

A traditional styrene separation unit for producing styrene by dehydrogenation of 500,000 tons of ethylbenzene is taken as an example. The styrene product column uses 0.04 MPaG steam as the heat source:

a) The pressure is 6 KPaA and the temperature was 63.56° C. at the top of the styrene product column T-104, the pressure at the column kettle is 8.6 KPaA, and the outlet temperature of the reboiler is 77.74° C.

b) The heat exchanger of the condenser of the styrene product column E-107 is of a BXM type with a diameter of 2,800 mm, a length of 6.000 mm of the heat exchange tube, a heat exchange area of 1,825 $m^2$, and a weight of 56.7 t. The styrene gas at the shell side is condensed by the circulating water at the tube side, the pressure drop at the shell side is 0.9 KPa, and the uncondensed gas-phase styrene at the outlet of the heat exchanger has a mass flow of 356 Kg/h.

c) The circulating water used for the condenser of the styrene product column E-107 is connected in series with the circulating water used for the condenser of the low pressure ethylbenzene/styrene column E-105, and the condenser of the styrene product column E-107 is placed in a front portion of the circulating water flow path, so as to increase the heat transfer temperature difference of the condenser of the low pressure ethylbenzene/styrene column E-105.

d) A thermosyphon heat exchanger is adopted for the styrene product column, and the required heat load is 8,083 kW. 0.04 PMPaG steam is consumed at 12.89 t/h. Two reboilers are needed to be connected in parallel. Each reboiler has a diameter of 2,200 mm, the heat exchange tube has a length of 3,000 mm, and each reboiler has a heat exchange area of 842 $m^2$. Each reboiler has a weight of 28.9 t.

e) The styrene product column T-104 has a diameter of 4,200 mm, the column shell has a weight of 75.4 t, and the packing volume is 249 $m^3$.

Comparing Application Example I with Comparative Example I

1. Application example I does not need to use steam, and only the shaft power consumed by the ethylbenzene heat pump compressor C-101 and the falling film reboiler circulating pump is added 594.4 kW in total. At the unit price of 0.7 yuan per kilowatt hour, it costs 416.08 yuan/hour. The energy consumption per hour is 594.4*0.086=51.1 kg standard oil/hour. 0.086 is a standard oil conversion coefficient of electricity in the "Norm of energy consumption per unit product of styrene monomer GB 32053". Note: The actual power consumption of the compressor and the circulating pump of the falling film reboiler in the Application Example I, Application Example II and Application Example III do not exceed 1.2 times of the shaft power.

2. For Comparative Example I, there is no need to increase power consumption, but 0.04 MPaG steam is needed to be used at 12.89 t/h. At the unit price of 100 yuan/ton, it costs 1,289 yuan/hour. The energy consumption per hour is 12.89*55=708.95 kg standard oil/hour. 55 is a standard oil conversion coefficient of low pressure steam in the "Norm of energy consumption per unit product of styrene monomer GB 32053".

3. The weight of the column, reboiler, and condenser in Application Example I is almost doubled and the investment increased by about 3 million yuan due to the lower column pressure compared with the traditional process in Application Example I. In addition, Application Example I requires an additional investment of 9.5 million yuan for the compressor and the circulating pump of the falling film reboiler compared with the traditional process. With other supporting expenses, the increased investment cost of Application Example I could be recovered in about two years.

Application Example II

A styrene separation unit for producing styrene by dehydrogenation of 500.000 tons of ethylbenzene is taken as an example. High-concentration gas-phase ethylbenzene distilled from the top of the low pressure ethylbenzene/styrene column T-103 is pressurized by the ethylbenzene heat pump compressor C-101, and only provides a heat source for the falling film reboiler of the pre-separation column E-101.

Figure 4:
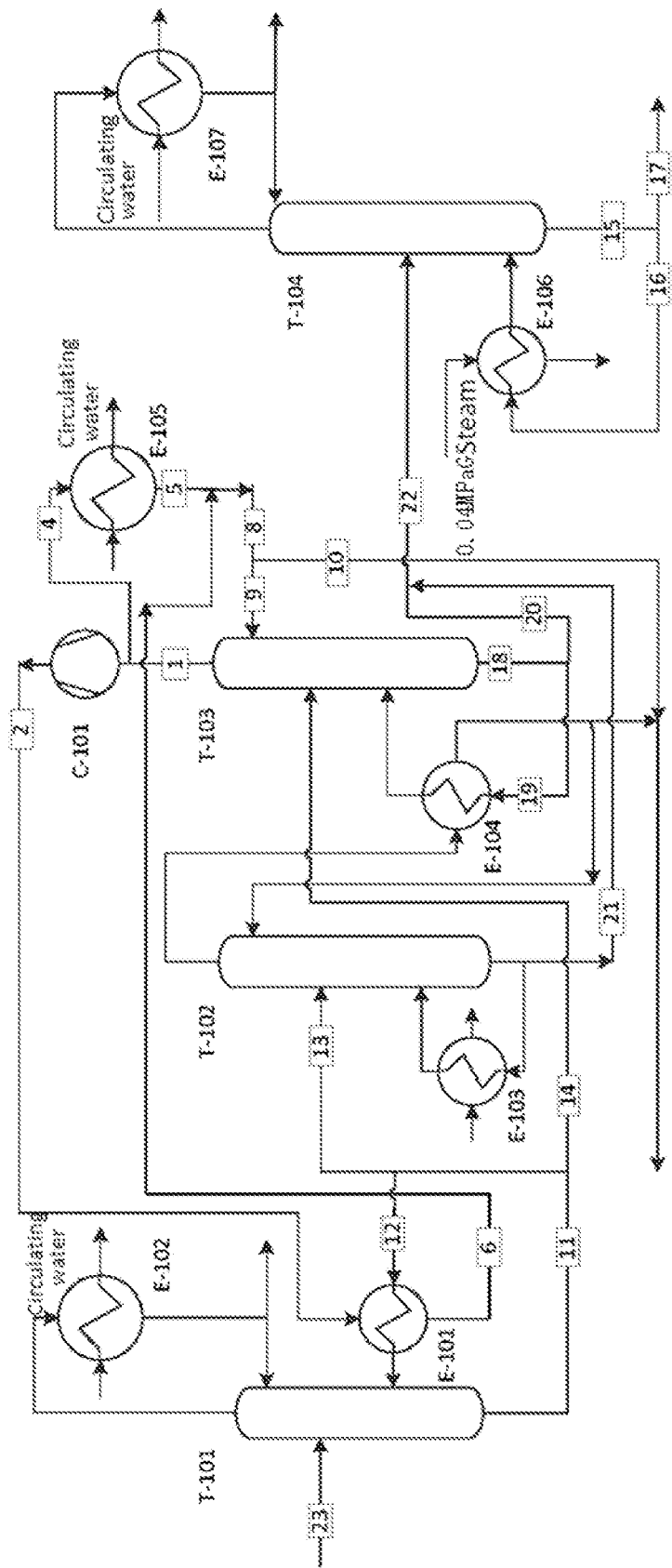
FIG. 4 is a route diagram of a styrene refining process route by using combined open heat pump technology and falling film reboilers to provide a heat source of a pre-separation column disclosed in Application Example II.

The specific process route is shown in FIG. 4.

a) The pressure is 10 KPaA and the temperature is 67.04° C. at the top of the low pressure ethylbenzene-styrene column T-103, and the high-concentration gas-phase ethylbenzene at the top of the low pressure ethylbenzene/styrene column is fed into the falling film reboiler of the pre-separation column E-101 at a flow rate 5 of 0.81 t/h after being pressurized by the ethylbenzene heat pump compressor C-101.

b) The pressure is 14 KPaA, the column top temperature is 46.6° C. at the top of the pre-separation column T-101, the pressure at the column kettle is 15.8 KPaA, and the outlet temperature of the falling film reboiler of the pre-separation column E-101 is 83.251° C.

c) Inlet conditions of the ethylbenzene heat pump compressor C-101: a pressure of 10 KPaA, a temperature of 67.04° C., and a flow rate of 50.81 t/h. Outlet conditions of the ethylbenzene heat pump compressor C-101: a pressure of 36 KPaA. The shaft power is 657.8 kW (efficiency of the ethylbenzene heat pump compressor is calculated as 75%).

d) The heat exchanger of the condenser of the pre-separation column E-102 is of a BXM type with a diameter of 2,500 mm, a length of 6,000 mm, a heat exchange area of 2,238 m$^2$, and a weight of 50.9 t. The styrene gas at the shell side is condensed by the circulating water at the tube side, the pressure drop at the shell side is 0.72 KPa, and the uncondensed gas phase at the outlet of the heat exchanger has a flow rate of 3,389 Kg/h.

e) The circulating water used for the condenser of the pre-separation column E-102 is connected in series with the circulating water used for the condenser of the low pressure ethylbenzene/styrene column E-105, and the condenser of the pre-separation column E-102 is placed in a front portion of the circulating water flow path, so as to increase the heat transfer temperature difference of the low pressure ethylbenzene/styrene column E-105.

f) A heat load required by the falling film reboiler of the pre-separation column E-101 is 4,948 kW. The falling film heat exchanger which is of a BEM type has a diameter of 3.000 mm, a length of 6,500 mm, a heat exchange area of 3,445 m$^2$, and a total volume of 90.9 t. The temperature difference is 8.5° C., the temperature at the shell side is 91.33-98.79° C., the temperature at the tube side is 83.4-86.78° C., the uncondensed non condensable gas volume at the shell side outlet has a flow rate of 1,316 Kg/h, and the gasification rate is 24.3%.

g) Circulating pump supporting for the falling film reboiler of the styrene product column has a design flow of 276.8 m$^2$/h (115% margin), a head of 36 m, and shaft power of 33 kW.

h) The pre-separation column T-101 has a diameter of 3,400 mm.

Comparative Example II

This comparative example was mainly compared with Application Example II:

A traditional styrene separation unit for producing styrene by dehydrogenation of 500,000 tons of ethylbenzene is taken as an example. The pre-separation column uses 0.04 MPaG steam as the heat source:

a) The pressure is 20 KPaA and the temperature is 55.18° C. at the top of the pre-separation column T-101, the pressure at the column kettle is 21.8 KPaA, and the outlet temperature of the reboiler is 91.94'.

b) The heat exchanger of the condenser of the pre-separation column E-102 is of a BXM type with a diameter of 2,200 mm, a length of 6,000 mm of the heat exchange tube, a heat exchange area of 1,553 m$^2$, and a weight of 38.5 t. The styrene gas at the shell side is condensed by the circulating water at the tube side, the pressure drop at the shell side is 0.58 KPa, and the uncondensed gas-phase styrene at the outlet of the heat exchanger had a mass flow of 1,710 Kg/h.

c) A thermosyphon heat exchanger is adopted for the pre-separation column, and the required heat load is 4,948 kW. 0.04 PMPaG steam is consumed at 7.92 t/2 h. Two reboilers are needed to be connected in parallel. Each reboiler has a diameter of 2,000 mm, the heat exchange tube has a length of 3,000 mm, and each reboiler has a heat exchange area of 712 m$^2$. Each reboiler has a weight of 26.1 t.

d) The pre-separation column T-101 has a diameter of 3,800 mm.

Comparing Application Example II with Comparative Example II

1. Application example II does not need to use steam, and only the shaft power consumed by the ethylbenzene heat pump compressor C-101 and the falling film reboiler circulating pump is added 690.8 kW in total. At the unit price of 0.7 yuan per kilowatt hour, it costs 483.56 yuan/hour. The energy consumption per hour is 690.8*0.086=59.4 kg standard oil/hour. 0.086 is a standard oil conversion coefficient of electricity in the "Norm of energy consumption per unit product of styrene monomer GB 32053".

2. For Comparative Example II, there is no need to increase power consumption, but 0.04 MPaG steam is needed to be used at 7.92 t/h. At the unit price of 100 yuan/ton, it costs 792 yuan/hour. The energy consumption per hour is 7.92*55=435.6 kg standard oil/hour. 55 is a standard oil conversion coefficient of low pressure steam in the "Norm of energy consumption per unit product of styrene monomer GB 32053".

3. The weight of the column, reboiler, and condenser in Application Example II is almost increased by 50% and the investment increased by about 1 million yuan due to the lower column pressure compared with the traditional process in Application Example U. In addition, Application Example II requires an additional investment of 7.5 million yuan for the compressor and the circulating pump of the falling film reboiler compared with the traditional process. With other supporting expenses, the increased investment cost of Application Example II could be recovered in about four years.

Application Example III

Figure 5:
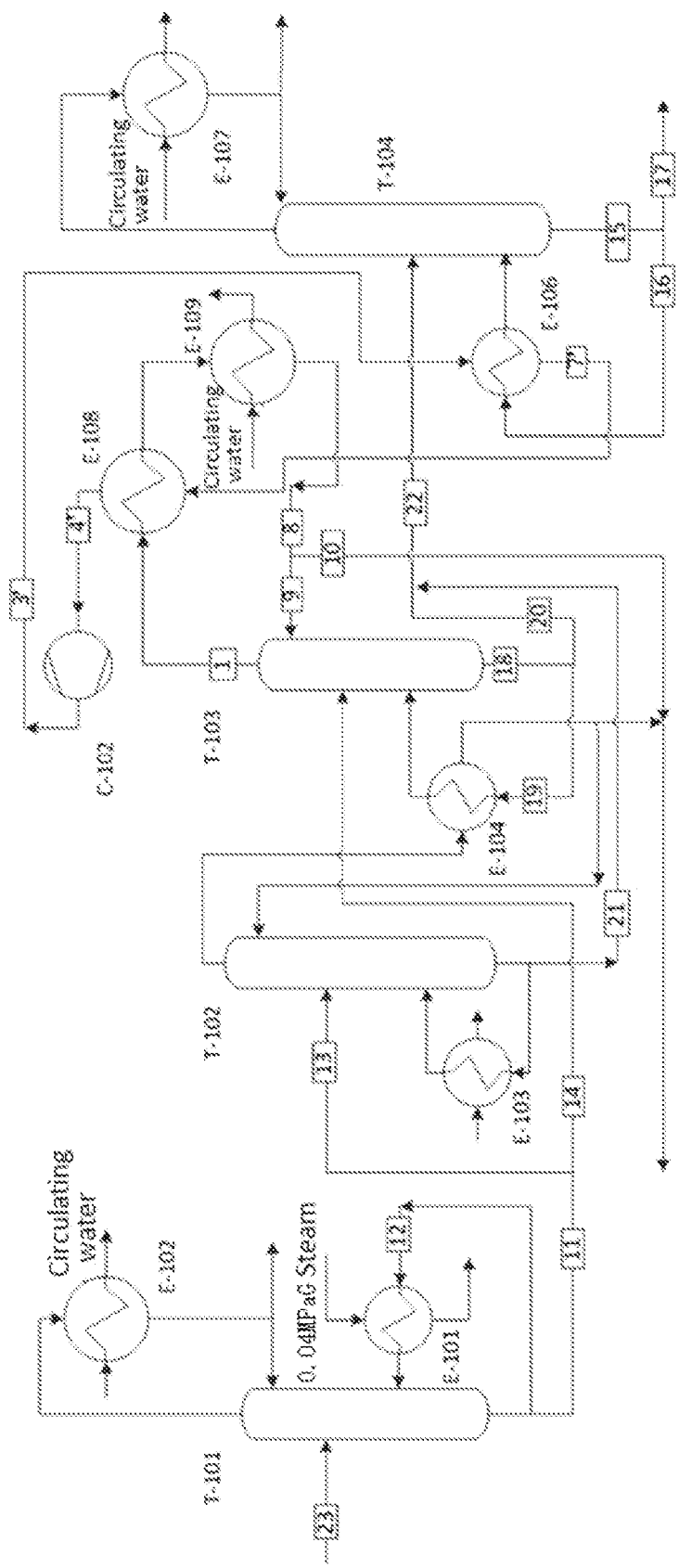
FIG. 5 is a route diagram of a styrene refining process by using combined closed heat pump technology and falling film reboilers to provide a heat source of a styrene product column disclosed in Application Example III.

A styrene separation unit for producing styrene by dehydrogenation of 500,000 tons of ethylbenzene is taken as an example. This application example uses the closed heat pump technology, the flow at the top of the low pressure ethylbenzene % styrene column T-103 is fed into the heat pump working medium evaporator of the low pressure ethylbenzene/styrene column E-108, and the uncondensed flow is continuously fed into the aftercondenser of the low pressure ethylbenzene/styrene separation column E-109 for condensation. A second heat pump working medium gas phase flow 3' obtained after the evaporated heat pump working medium 4' is pressurized by the working medium heat pump compressor C-102 is fed into the falling film reboiler of the styrene product column E-106 as the heat source. The second condensing heat pump working medium 7' condensed in the falling film reboiler of the styrene product column E-106 is recycled back to the heat pump working medium evaporator of the low pressure ethylbenzene/styrene column E-108 for further gasification and recycling. Details are shown in FIG. 5.

a) The pressure is 9.99 KPaA and the temperature is 66.96° C. at the top of the low pressure ethylbenzene/styrene column T-103, and the high-concentration gas-phase ethylbenzene at the top of the low pressure ethylbenzene/styrene column is fed into the heat pump working medium evaporator of the low pressure ethylbenzene/styrene column E-108 at a flow rate of 69.3 t/h.

b) The pressure is 2.5 KPaA and the column top temperature is 45.45° C. at the top of the styrene product column T-104, the pressure at the column kettle is 5.6 KPaA, and the outlet temperature of the falling film reboiler of the styrene product column E-106 is 67.5° C.

c) Inlet conditions of the working medium heat pump compressor C-102: a medium of 1-butene, a pressure of 748 KPaA, a temperature of 58° C., and a flow rate of 88.5 t/h. Outlet conditions of the working medium heat pump compressor C-102: a pressure of 1,150 KPaA. The shaft power was 696.5 kW (efficiency of the working medium heat pump compressor is calculated as 65%).

d) The heat exchanger of the condenser of the styrene product column E-107 is of a BXM type with a diameter of 4,000 mm, a length of 7,000 mm, a heat exchange area of 3,008 m$^2$, and a weight of 101.8 t. The styrene gas at the shell side is condensed by the circulating water at the tube side, the pressure drop at the shell side is 0.4 KPa, and the uncondensed gas phase styrene at the outlet of the heat exchanger has a mass flow of 725 Kg/h.

e) The heat exchanger of the heat pump working medium evaporator of the low pressure ethylbenzene/styrene column E-108 is of a BKM type with a diameter of 2,500 mm, a length of 7,000 mm, a heat exchange area of 2,785 m$^2$ and a weight of 71.98 t. The temperature of 1-butene gasification at the shell side is 57.99° C., the inlet temperature of the high-concentration gas-phase ethylbenzene at the tube side is 66.9° C., the outlet temperature at the tube side was 60° C., and the uncondensed 1-butene gasification gas at the outlet of the tube side has a flow rate of 1,871 Kg/h.

f) The circulating water used for the condenser of the styrene product column E-107 is connected in series with the circulating water used for the aftercondenser of the low pressure ethylbenzene/styrene column E-109, and the condenser of the styrene product column E-107 is placed in a front portion of the circulating water flow path, so as to increase the heat transfer temperature difference of the aftercondenser of the low pressure ethylbenzene/styrene column E-109.

g) A heat load required by the falling film reboiler of the styrene product column E-106 was 8,059 kW. The falling film heat exchanger which is of a BEM type has a diameter of 4,000 mm, a length of 8,500 mm, a heat exchange area of 4,019 m$^2$, and a total volume of 156.8 t. The temperature difference is 6.2° C., the temperature at the shell side is 80.35-75.00° C., the temperature at the tube side is 67.5-70.16° C., the uncondensed gas volume at the outlet of the shell side has a mass flow of 0 Kg/h, and the gasification rate was 12%.

h) Circulating pump supporting for the falling film reboiler of the styrene product column E-106 has a design flow of 707 m$^2$/h (115% margin), a head of 36 m, and shaft power of 85 kW.

i) The styrene product column T-104 has a diameter of 5,000 mm, the column shell has a weight of 103.8 t, and the packing volume is 353 m.

Comparative Example III

A traditional styrene separation unit for producing styrene by dehydrogenation of 500,000 tons of ethylbenzene is taken as an example. The styrene product column uses 0.04 MPaG steam as the heat source:

a) The pressure is 6 KPaA and the temperature is 63.56° C. at the top of the styrene product column T-104, the pressure at the column kettle is 8.6 KPaA, and the outlet temperature of the reboiler is 77.74° C.

b) The heat exchanger of the condenser of the styrene product column E-107 is of a BXM type with a diameter of 2,800 mm, a heat exchange tube length of 6,000 mm, a heat exchange area of 1,825 m$^2$, and a weight of 56.7 t. The styrene gas at the shell side is condensed by the circulating water at the tube side, the pressure drop at the shell side is 0.9 KPa, and the uncondensed gas-phase styrene at the outlet of the heat exchanger has a mass flow of 356 Kg/h.

c) A thermosyphon heat exchanger is adopted for the styrene product column, and the required heat load is 8,083 kW. 0.04 PMPaG steam is consumed at 12.89 t/h. Two reboilers are needed to be connected in parallel. Each reboiler has a diameter of 2,200 mm, the heat exchange tube has a length of 3,000 mm, and each reboiler has a heat exchange area of 842 m$^2$. Each reboiler has a weight of 28.9 t.

d) The styrene product column T-104 has a diameter of 4,200 m$^2$, the column shell has a weight of 75.4 t, and the packing volume is 249 m$^3$.

Comparing Application Example III with Comparative Example III

1. Application example HI does not need to use steam, and only the shaft power consumed by the working medium heat pump compressor C-102 and the falling film reboiler circulating pump is added 781.5 kW in total. At the unit price of 0.7 yuan per kilowatt hour, it costs 547.05 yuan/hour. The energy consumption per hour is 781.5*0.086=67.21 kg standard oil/hour. 0.086 is a standard oil conversion coefficient of electricity in the "Norm of energy consumption per unit product of styrene monomer GB 32053".

2. For Comparative Example III, there is no need to increase power consumption, but 0.04 MPaG steam is used at 12.89 t/h. At the unit price of 100 yuan/ton, it costs 1,289 yuan/hour. The energy consumption per hour is 12.89*55=708.95 kg standard oil/hour. 55 is a standard oil conversion coefficient of low pressure steam in the "Norm of energy consumption per unit product of styrene monomer GB 32053".

3. The weight of the column, reboiler, and condenser in Application Example III is almost doubled due to the lower column pressure compared with the traditional process in Application Example III, and the heat pump working medium evaporator of the low pressure ethylbenzene/styrene column E-108 is added. The investment increased by about 4 million yuan. In addition. Application Example III requires an additional investment of 8.5 million yuan for the compressor and the circulating pump of the falling film reboiler compared with the traditional process. With other supporting expenses, the increased investment cost of Application Example I could be recovered in about 2.5 years.

To sum up, the present disclosure realizes the thermal coupling between the low pressure ethylbenzene/styrene column T-103, the pre-separation column T-101, and the styrene product column T-104 by increasing the heat pump cycle process and combining the use of the falling film reboilers, which can further greatly reduce the energy consumption in the styrene separation process on the basis of the energy-saving technology of coupled high and low pressure ethylbenzene/styrene separation columns, can recover the investment cost after several years of operation, and has remarkable long-term economic and environmental benefits.

The foregoing displays and describes the basic principles, the main features and the advantages of the present disclosure. However, the above are only specific examples of the present disclosure, and the technical features of the present disclosure are not limited to this. Any other implementations obtained by those skilled in the art without departing from the technical solution of the present disclosure should be covered by the patent scope of the present disclosure.

What is claimed is:

1. A method for refining styrene by using combined falling film reboilers and heat pump technology to provide a heat source of a separation column, wherein a refining route from upstream to downstream comprises a pre-separation column, a high pressure ethylbenzene/styrene column, a low pressure ethylbenzene/styrene column, and a styrene product column, and a total flow at a kettle of the pre-separation column from a bottom of the pre-separation column is divided into two streams, wherein one of the two streams is fed into the high pressure ethylbenzene/styrene column and the other of the two streams is fed into the low pressure ethylbenzene/styrene column;

ethylbenzene flows separated from tops of the high pressure ethylbenzene/styrene column and the low pressure ethylbenzene/styrene column are fed into a ethylbenzene dehydrogenation unit as a raw material, and flows from corresponding kettles are fed into the styrene product column;

a flow of tar with styrene not completely removed in a kettle of the styrene product column is fed into a styrene recovery system;

a mixture of benzene and toluene separated from a top of the pre-separation column is continuously separated to obtain benzene returned to an ethylbenzene unit as a raw material and toluene as a by-product;

the low pressure ethylbenzene/styrene column is connected to a reboiler of the low pressure ethylbenzene/styrene column, a product flow of the low pressure ethylbenzene/styrene column obtained from a bottom of the low pressure ethylbenzene/styrene column is fed into the styrene product column, and a circulation flow of the low pressure ethylbenzene/styrene column flows through the reboiler of the low pressure ethylbenzene/styrene column and is partially gasified through heating by a gas phase flow distilled from the top of the high pressure ethylbenzene/styrene column and then returned to the bottom of the low pressure ethylbenzene/styrene column; and the high pressure ethylbenzene/styrene column is connected to a reboiler of the high pressure ethylbenzene/styrene column, a product flow of the high pressure ethylbenzene/styrene column from a bottom of the high pressure ethylbenzene/styrene column is fed into the styrene product column, and a distillate from the top of the high pressure ethylbenzene/styrene column is fed into the reboiler of the low pressure ethylbenzene/styrene column;

wherein an open heat pump cycle or a closed heat pump cycle is set at the top of the low pressure ethylbenzene/styrene column;

wherein the pre-separation column is provided with a reboiler with a gas phase medium fed by an open or closed heat pump as a heat source;

wherein the styrene product column is provided with a reboiler with a gas phase medium fed by the open or closed heat pump as a heat source;

wherein the open heat pump cycle is as follows: the top of the low pressure ethylbenzene/styrene column is connected to an ethylbenzene heat pump compressor, and part of a gas phase flow from the top of the low pressure ethylbenzene/styrene column is compressed by the ethylbenzene heat pump compressor and then configured as a heat source of the pre-separation column and/or the styrene product column; and another part of the gas phase flow that is unpressurized is fed into a condenser of the low pressure ethylbenzene/styrene column for condensation, condensate and a flow condensed by the reboiler of the pre-separation column and/or the reboiler of the styrene product column are collected together and pressurized as a total condensate flow, part of the total condensate flow is configured as reflux of the low pressure ethylbenzene/styrene column, and a remaining part of the total condensate is sent to the ethylbenzene dehydrogenation unit for recycling as a extracted flow;

wherein the closed heat pump cycle is as follows: the gas phase flow at the top of the low pressure ethylbenzene/styrene column is fed into a heat pump working medium evaporator of the low pressure ethylbenzene/styrene column as a heat source for evaporation of a heat pump working medium, and an uncondensed flow is continuously fed into an aftercondenser of the low pressure ethylbenzene/styrene column for condensation; and the evaporated heat pump working medium is pressurized by a working medium heat pump compressor and fed into the reboiler of the pre-separation column and/or the reboiler of the styrene product column as a heat source, and a heat pump working medium condensed by the reboiler of the pre-separation column and/or the reboiler of the styrene product column is recycled back to the heat pump working medium evaporator of the low pressure ethylbenzene/styrene column; and wherein the reboiler on the pre-separation column, the reboiler on the styrene product column, and the low pressure ethylbenzene/styrene reboiler are all falling film reboilers.

2. The method for refining styrene by using falling film reboilers and heat pump technology to provide a heat source of a separation column according to claim 1, wherein the ethylbenzene heat pump compressor and the working medium heat pump compressor are jointly arranged, and provide heat for the reboiler of the pre-separation column and the reboiler of the styrene product column simultaneously; or alternatively, compressors with different outlet pressures are arranged independently according to different condensing pressures required by heat source sides of the reboiler of the pre-separation column and the reboiler of the styrene product column.

3. The method for refining styrene by using falling film reboilers and heat pump technology to provide a heat source of a separation column according to claim 1, wherein both the falling film reboiler of the pre-separation column and the falling film reboiler of the styrene product column are equipped with a circulating pump to establish a circulation flow required by the falling film reboilers.

4. The method for refining styrene by using falling film reboilers and heat pump technology to provide a heat source of a separation column according to claim 1, wherein the top of the pre-separation column is connected to a condenser of the pre-separation column, a top of the styrene product column is connected to a condenser of the styrene product column, and both the condenser of the pre-separation column and the condenser of the styrene product column utilize circulating water as a cold source.

5. The method for refining styrene by using falling film reboilers and heat pump technology to provide a heat source of a separation column according to claim 4, wherein in the open heat pump cycle, the circulating water for the condenser of the styrene product column and the condenser of the pre-separation column is connected in series with circulating water for the condenser of the low pressure ethylbenzene/styrene column, and both the condenser of the styrene product column and the condenser of the pre-separation column are placed in a front portion of a circulating water flow path.

6. The method for refining styrene by using falling film reboilers and heat pump technology to provide a heat source of a separation column according to claim 4, wherein in the closed heat pump cycle, the circulating water for the condenser of the styrene product column and the condenser of the pre-separation column is connected in series with circulating water for the aftercondenser of the low pressure ethylbenzene/styrene column, and both the condenser of the styrene product column and the condenser of the pre-separation column are placed in a front portion of a circulating water flow path.

7. The method for refining styrene by using falling film reboilers and heat pump technology to provide a heat source of a separation column according to claim 1, wherein the low pressure ethylbenzene/styrene column has an operating pressure of 7-17 KPaA.

8. The method for refining styrene by using falling film reboilers and heat pump technology to provide a heat source of a separation column according to claim 1, wherein the pre-separation column has an operating pressure of 12-19 KPaA.

9. The method for refining styrene by using falling film reboilers and heat pump technology to provide a heat source of a separation column according to claim 1, wherein the styrene product column has an operating pressure of 2-5 KPaA.

* * * * *